United States Patent [19]

Esders et al.

[11] 4,179,334

[45] Dec. 18, 1979

[54] HYDROLYSIS OF PROTEIN-BOUND TRIGLYCERIDES

[75] Inventors: Theodore W. Esders, Webster; Charles T. Goodhue, Rochester; Christine A. Michrina, Webster, all of N.Y.

[73] Assignee: Eastman Kodak Company, Rochester, N.Y.

[21] Appl. No.: 715,798

[22] Filed: Aug. 19, 1976

[51] Int. Cl.² ............................................. G01N 31/14
[52] U.S. Cl. ..................................... 195/30; 435/21; 435/69; 435/921; 435/822; 435/134
[58] Field of Search ................. 195/99, 103.5 R, 63, 195/30, 127

[56] References Cited

U.S. PATENT DOCUMENTS

| | | | |
|---|---|---|---|
| 3,759,793 | 9/1973 | Stork et al. | 195/103.5 R |
| 3,862,009 | 1/1975 | Wahlefeld | 195/103.5 R |
| 3,894,844 | 7/1975 | Pinto et al. | 23/230 B |
| 3,898,130 | 8/1975 | Komatsu | 195/103.5 R |
| 3,992,158 | 11/1976 | Przybylowicz et al. | 195/103.5 R |
| 4,013,512 | 3/1977 | Kosugi et al. | 195/66 R |

*Primary Examiner*—Alvin E. Tanenholtz
*Attorney, Agent, or Firm*—Ronald P. Hilst

[57] ABSTRACT

A novel process is described for hydrolyzing protein-bound triglycerides such as blood serum triglycerides comprising contacting sample containing protein-bound triglycerides with a compatible mixture of an enzyme preparation which demonstrates triglyceride hydrolase activity and, as an effector, a surfactant.

Hydrolysis compositions comprising compatible mixtures of an enzyme preparation which demonstrates triglyceride hydrolase activity and an effector which is a surfactant are also described, as are analytical elements comprising at least one layer which includes a hydrolysis composition which comprises such a compatible mixture of an enzyme preparation which demonstrates triglyceride hydrolase activity and a surfactant.

25 Claims, 2 Drawing Figures

HYDROLYSIS OF PROTEIN-BOUND TRIGLYCERIDES

FIELD OF THE INVENTION

The present invention relates to methods for the hydrolysis of lipids and more particularly to methods and compositions for the hydrolysis of protein-bound lipids such as serum triglycerides, cholesterol esters and phospholipids.

BACKGROUND OF THE INVENTION

In the assay of body fluids, especially blood serum, for triglyceride concentration, the initial step requires hydrolysis of triglycerides, for example, hydrolysis of triglycerides to glycerol.

Conventional procedures for triglyceride hydrolysis use a strong base (KOH, NaOH, etc.), or for reasons of simplicity and selectivity, a hydrolase enzyme (i.e., a lipase). Handling of caustic materials may be inconvenient or undesirable and, as discussed in relation to prior publications below, enzymatic techniques can be useful for the hydrolysis of "free" triglycerides, i.e., those not bound to protein, but are either ineffective or very slow when used to treat protein-bound triglycerides. The binding of the triglyceride to protein apparently inhibits the action of the hydrolase and thus requires some means for breaking the protein-triglyceride complex before the hydrolase can act on the triglyceride.

U.S. Pat. No. 3,703,591 to Bucolo et al describes the use of a combination of a lipase and a protease to achieve serum (i.e., protein-bound) triglyceride hydrolysis. No suggestion is made to use a surfactant either in combination with or as a substitute for the protease.

U.S. Pat. No. 3,759,793 to Stork et al describes the hydrolysis of serum triglycerides using a lipase from *Rhizopus arrhizus* which is apparently identical to that suggested by Bucolo et al, however, with no requirement for a protease. The reasons for this apparent anomaly are not clear, however, it is noted in British Pat. No. 1,395,126 of the same assignee that the Stork et al hydrolysis technique is very slow. This British Patent describes an improved method for hydrolyzing triglycerides with the aforementioned *Rhizopus arrhizus* lipase comprising contacting the triglyceride with the lipase in a buffer and in the presence of carboxylesterase and an alkali metal or alkaline earth metal alkyl sulfate, the alkyl radical of which contains 10 to 15 carbon atoms. In support of the patentability of this technique this patent cites the slowness of earlier enzymatic techniques, specifically those of Stork et al. The preferred alkyl sulfate is sodium dodecyl sulfate. There is no suggestion that the use of surfactant alone in the absence of carboxylesterase stimulates lipase activity and in fact, as will be shown in the examples below, the use of at least some of the stimulating surfactants described herein actually inhibit the activity of lipase from *Rhizopus arrhizus*.

Helenius, Ari and Simons, Kai, Biochemistry, Vol. 10, No. 13 (1971) describe a method for removing all major lipids from human plasma low-density lipoprotein comprising treatment of the human plasma with high concentrations of natural and synthetic surfactants. Lipid removal is applied for purposes of characterizing the lipid free protein moiety of human plasma low-density lipoprotein. There is no suggestion in this publication that the combination of a surfactant and a lipase would yield a useful analytical tool which would simplify the assay of serum for triglyceride content by providing a fast and accurate hydrolysis method and stable assay compositions.

U.S. Pat. No. 3,689,364 issued Sept. 5, 1972 describes an assay for lipase contained in body fluids such as blood serum using a "free" triglyceride emulsion as substrate for the lipase. It is suggested that the bile salts which stabilize the substrate emulsion of "free" triglyceride (i.e., triglycerides not bound to protein) also concurrently exert an "activating effect" on the lipase under assay when it is a pancreatic lipase. The activating effect apparently results in an increase in the hydrolytic activity of the lipase on the free triglycerides of the substrate emulsion. There is no teaching or suggestion in this patent that such bile salts exert any effect on lipase preparations when contacted with lipids bound to proteins as are found in blood serum.

U.S. Pat. No. 3,898,130 to Komatsu issued Aug. 5, 1975 describes a method for hydrolyzing triglycerides comprising contacting triglyceride with a composition comprising a mixture of a microbial lipase, particularly Candida lipase, a pancreatic lipase and a bile salt. Both the microbial and the pancreatic lipase enzymes are critical components of the hydrolysis composition.

German Offenlegungsschrift No. 2,522,432 published Dec. 4, 1975 describes an enzymatic method for hydrolyzing cholesterol esters using a cholesterol esterase from *Pseudomonas fluorescens*.

U.S. Pat. No. 3,925,164 issued Dec. 9, 1975 describes a method for hydrolyzing cholesterol esters using a cholesterol esterase from *Candida rugosa*, Rhizopus and Aspergillus. It is suggested that the addition of a surfactant increases the activity of the esterase.

SUMMARY OF THE INVENTION

It has now been discovered that protein-bound triglycerides can be hydrolyzed in relatively short times on the order of less than about 10 minutes (preferably in about 5 minutes) by contacting the protein-bound triglyceride with a compatible mixture of a lipase preparation which demonstrates triglyceride hydrolase activity and an effector which is a surfactant.

The techniques and compositions described herein permit the use of a much broader range of lipase materials as hydrolyzing agents than has been possible with prior art methods. Thus, lower cost materials can be used to attain reaction times and states of reaction completeness at least equal to those attainable with the prior art methods and materials.

DESCRIPTION OF THE PREFERRED EMBODIMENTS

Figure 1:
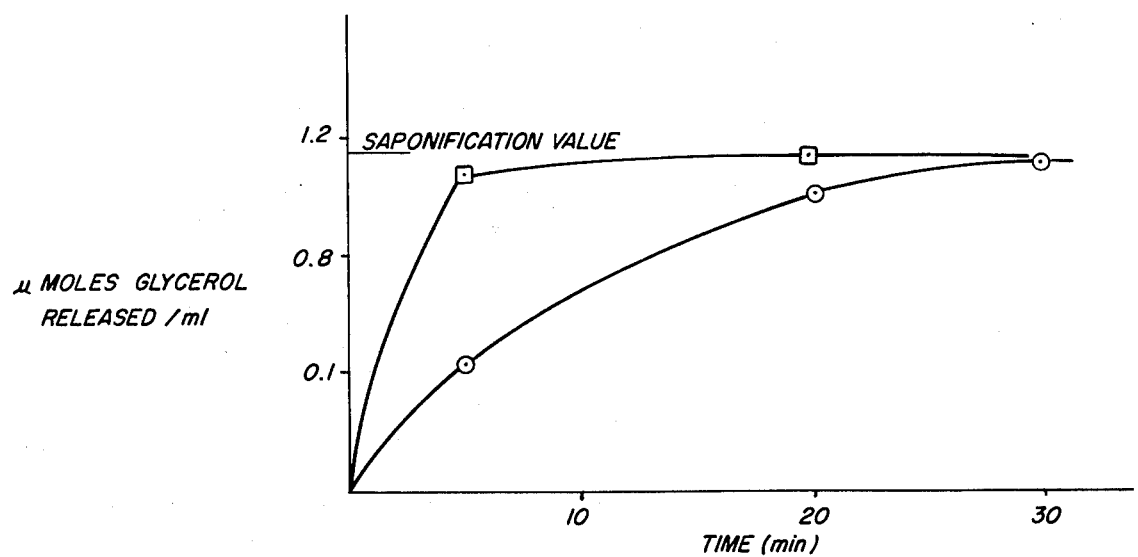
Figure 2:
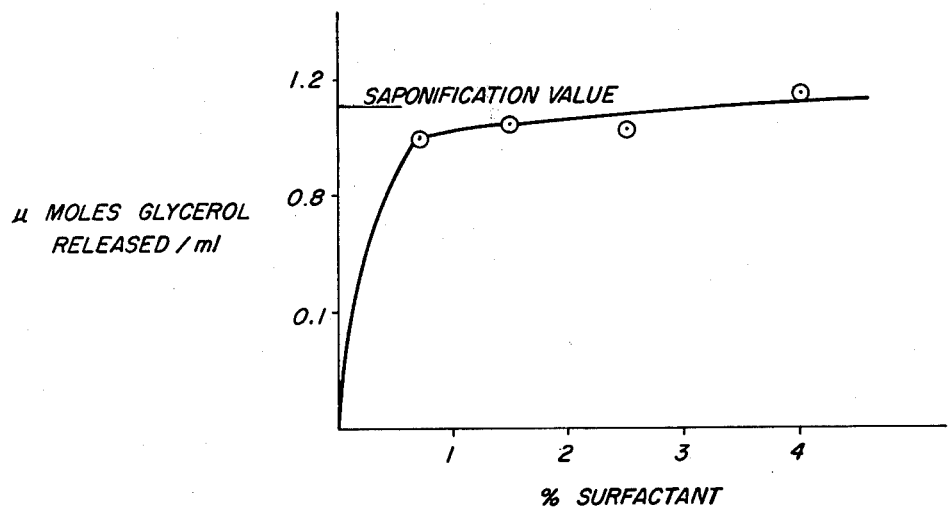

As discussed hereinabove, there are a large number of enzyme preparations, particularly lipases, which, although they catalyze the hydrolysis of free triglycerides, are apparently incapable of catalyzing the hydrolysis of triglycerides bound to protein, as found in blood serum. This result is apparently due to some effect of the protein-lipid bond which prevents the lipase from catalyzing the hydrolysis in the usual fashion. The prior art has suggested the use of what might be termed effectors, namely, agents which increase the rate at which lipase materials can hydrolyze protein-bound lipids. Although the mechanism by which such agents act is not known, it is theorized that they attack the protein bonds in some way to "free" the triglyceride for hydrolysis in a conventional mode. Protease enzymes are known for this purpose.

We have found that certain surfactants are effectors and may be used as substitutes for protease to render useful as hydrolyzers of protein-bound triglyceride enzyme preparations which are normally incapable of catalyzing the hydrolysis of triglycerides or which catalyze such hyrolysis only at undesirably slow rates. Furthermore, since protease tends to degrade proteinaceous binders such as gelatin which are useful in multilayer elements for the detection of analyte as described in Belgian Pat. No. 801,742. The compositions described herein are particularly useful in such elements.

The novel hydrolysis compositions of the present invention thus consist essentially of a compatible mixture of an enzyme preparation which demonstrates triglyceride hydrolysis activity and an effector which is a surfactant.

Enzyme preparations useful in the methods and compositions described herein are those demonstrating free (i.e., not protein-bound) triglyceride hydrolytic activity. Lipase preparations which demonstrate such activity are specifically preferred.

By their very nature lipase preparations will catalyze the hydrolysis of free triglycerides. Hence, substantially any lipase preparation is a suitable candidate for use in the successful practice of the present invention.

Useful enzyme preparations for triglyceride hydrolysis may be derived from plant or animal sources but we prefer preparations from microbial sources such as from *Candida rugosa, Chromobacterium viscosum*, variant *paralipolyticum*, crude or purified. Other useful enzyme preparations and methods for their preparation are described in the following U.S. Pat. Nos. 2,888,385 to Grandel issued May 26, 1959; 3,168,448 to Melcer et al issued Feb. 2,1965, 3,189,529 to Yamada et al issued June 15,1965; 3,262,863 to Fukumoto et al issued July 26, 1966; and 3,513,073 to Mauvernay et al issued May 19, 1970.

Specifically preferred commercial enzyme preparations include wheat germ lipase from Miles Laboratories of Elkhart, Indiana, Lipase 3000 from Wilson Laboratories, Stepsin from Sigma Chemical Company (both of the latter are pancreatic enzymes), and Lipase M (from *Candida rugosa*) from Enzyme Development Company.

In theory, any surfactant is a suitable candidate for use in the successful practice of the present invention.

Certain surfactants, however, inhibit the hydrolase activity of certain enzyme preparations. For example, microbial enzyme from *Rhizopus arrhizus* is inhibited by octyl phenoxy polyethoxy ethanol surfactants. Consequently, it is important that before any attempt is made to combine an enzyme preparation and a surfactant for use as described herein some determination of the compatibility of the two members of the composition be made. Such a determination is preferably made by using the test described below. An enzyme preparation and surfactant mixture which successfully meets this test is referred to herein as a compatible mixture and each member thereof is said to be compatible with the other.

Hydrolysis compositions of the present invention are characterized by the following test. The proposed surfactant under evaluation is added to unbuffered reconstituted serum (specifically Validate, a serum standard available from General Diagnostics Division of Warner Lambert Company, Morris Plains, N.J.) at varying concentrations of between about 0 and 10% by weight and the solution incubated for about 5 minutes at 37° C. At this time, a sample of a proposed enzyme preparation is added and incubation continued for a period of about 20 minutes. Aliquots (~0.2 ml) of this solution are then diluted to 1.6 ml with water (containing 1.3 mM $CaCl_2$ to aid precipitate formation), placed in a boiling water bath for 10 minutes and centrifuged to clarify (0°, 37,000 Xg, 10 minutes). Glycerol in a 0.4 ml aliquot of the clear supernatant is quantified in a total volume of 1.2 ml by the method described by Garland, P.J. and Randle, P.B., Nature, 196, 987–988 (1962). A similar "control" test is performed concurrently using only the enzyme preparation without the surfactant. Any composition which stimulates release of amounts of glycerol greater than those released by the control is considered useful. When performing the foregoing test it is most desirable to run a blank which contains all of the components of the mixture but the enzyme preparation so that any reaction which may be due to free glycerol or other components of the serum can be subtracted. The preferred compositions accomplish hydrolysis of at least about 70% of the available triglyceride in less than 10 minutes and most preferred are those which achieve substantially complete hydrolysis, i.e., hydrolysis of at least about 90% of the available triglyceride in less than about 10 minutes.

Among the surfactants which have been found useful to stimulate the hydrolase activity of the foregoing useful enzyme preparations are nonionic and anionic surfactants including many of the natural surfactants such as the bile salts including deoxycholate, chenodeoxycholate, cholate and crude bile salt mixtures and synthetic surfactants such as sodium salts of alkylaryl polyether sulfonates commercially available from Rohm and Haas Company as Triton X-200 and Alkanol XC commercially available from E.I. duPont Corporation, alkyl phenoxy polyethoxy ethanols such as those available commercially from Rohm and Haas Company under the tradenames Triton X-114, 100, 102 and Triton n-101. Synthetic surfactants are preferred due to the large selection of available such materials and the ability to tailor surfactants to meet specific needs and requirements. Preferred alkyl phenoxy polyethoxy ethanols comprise a polyoxyethylene chain of less than about 20 oxyethylene units and have a hypophilic-lipophilic balance number below about 15. Other useful surfactants are presented in the examples below.

As will be demonstrated from the examples below, numerous surfactants which were evaluated did not produce acceptably high dissociation when combined with particular lipase preparations evaluated. This list included sodium dodecyl sulfate which is referred to in above-mentioned British Pat. No. 1,395,126. Exemplary hydrolysis compositions are shown in Table I.

The concentration of enzyme preparation and surfactant in the compatible mixtures useful for hydrolysis according to the methods described herein can vary greatly depending, for example, on such factors as the purity of the enzyme preparation, the activity of the enzyme preparation, the nature of the bound triglyceride, the particular surfactant used, etc. Generally, however, surfactant concentrations of from about 0.25 to about 10% by weight of the analytical solution have been found useful with concentrations of between about 0.5 and 5% by weight of surfactant providing optimum results. The useful range of concentrations of enzyme preparation will vary similarly, but concentrations of between about 10 and 80 mg/ml of the total analytical solution have been found quite useful when commercial preparations are used. Optimization of any such composition is, of course, within the skill of the art.

It should be apparent that hydrolysis compositions of the type described herein can be incorporated into any of the single or multiple layer bibulous or other analytical elements (for example, test papers) described in the prior art and that the use of the compositions and methods described herein in such elements for the detection or determination of protein-bound lipids is within the scope of the appended claims.

In accordance with one preferred embodiment, the hydrolysis compositions described herein are incorporated into one or more layers of multilayer analytical elements of the type described, for example, in Belgian Patent No. 801,742 and U.S. Pat. No. 3,992,158 issued Nov. 16, 1976. Such elements are intended to analyze liquids for the presence of a predetermined analyte and they include a preferably non-fibrous spreading layer, to deliver a uniform apparent concentration of analysis-active components in an applied sample to a reagent layer which contains at least some of the materials interactive in the presence of analyte to produce a detectable product. Such layers are in fluid contact under conditions of use.

Reference herein to fluid contact between layers in an analytical element identifies the ability of a fluid, whether liquid or gaseous, to pass in such element between superposed regions of the spreading layer and the reagent layer. Stated in another manner, fluid contact refers to the ability of components of a fluid to pass between the layers in fluid contact. Although such layers in fluid contact can be contiguous, they may also be separated by intervening layers as described in detail hereinafter. However, layers in the element that physically intervene a spreading layer and reagent layer in mutual fluid contact will not prevent the passage of fluid between the fluid contacting spreading and reagent layers.

Fluid contact between layers can be achieved by preparing elements having layers that are initially contiguous or effectively so for purposes of fluid passage. Alternatively, it may be appropriate to prepare elements that have layers initially non-contiguous, and which further can be spaced apart, such as by the use of interleaves as described, for example, in U.S. Pat. No. 3,511,608 or by the use of a resilient absorbent material or deformable supports as described in U.S. Pat. No. 3,917,453 and U.S. Pat. No. 3,933,594. As will be appreciated, if the element has initially non-contiguous layers, it may be necessary to apply compressive force or otherwise provide means to bring layers of the element into fluid contact at the time of its use to provide an analytical result.

According to a highly preferred embodiment of such an element, the hydrolysis composition described herein is incorporated into the spreading layer and a detection system, for example, NAD+ and glycerol dehydrogenase for triglyceride detection is included in the reagent layer.

The following description of standardized procedures and examples are presented to further illustrate the useful scope of the present invention.

Standard Procedures

Quantification of Glycerol Released by Hydroysis of Serum Triglycerides

Incubation mixtures comprise a final volume of 1–1.5 ml of a mixture of (1) buffer, (2) an aliquot of serum or serum substitute as a source of triglyceride (final triglyceride concentration was 1–1.6 $\mu$moles/ml), (3) a possible effector of the hydrolytic reaction, and (4) lipase preparation which was added to initiate the reaction after the other components had equilibrated at 37° C. Samples are incubated at 37° C. for an appropriate time, then aliquots (0.2 ml) are diluted to 1.6 ml with water (containing 1.3 mM $CaCl_2$ to aid precipitate formation when serum was used as substrate), placed in a boiling water bath for ten minutes, and centrifuged to clarify (0°, 37,000 Xg, 10 min.). Glycerol in a 0.4 ml aliquot (41–67 nmoles assuming complete hydrolysis) of the clear supernatant is quantified in a total volume of 1.2 ml by the method of Garland and Randle described at NATURE, 196, 987–988 (1962). Glycerol kinase, pyruvate kinase, lactate dehydrogenase, ATP, $MgSO_4$, phosphoenolpyruvate and NADH are all present in excess. The glycerol concentration is stoichiometrically related to NADH oxidation which is determined spectrophotometrically at 340 nm. In all cases, reagent blanks and any reaction attributed to free glycerol or other components in serum have been subtracted. Hence, the results represent glycerol released by the hydrolytic reaction. (Blanks contained all components except lipase).

Control Procedures

Saponification of Triglycerides—A 0.2 ml sample to be saponified was added to a screwtop test tube, along with 0.5 ml of 0.5 N ethanolic KOH, and the tube incubated for 30 minutes at 70° C. The sample was then cooled, and 1.0 ml of 0.15 M $MgSO_4$ added. After centrifugation, the glycerol content of 0.2 ml of the clear supernatant was determined in a total volume of 1.2 ml by the method of Garland and Randle. Serum and ethanolic-KOH reagent blanks were subtracted to determine triglyceride glycerol.

(In all examples lipase from *C. rugosa* was used.)

EXAMPLE 1—Rate of Lipase Catalyzed Hydrolysis of Serum Triglycerides in the Presence of Nonionic Surfactant or $\alpha$-Chymotrypsin Octyl phenoxy polyethoxy ethanol (Triton X-100), final concentration 0.7%) or $\alpha$-chymotrypsin (protease), final concentration 20 mg/ml was added to unbuffered reconstituted serum and after equilibration at 37° C. for one minute, the reaction was initiated by lipase addition (final concentration 40 mg/ml). At the time indicated, the reaction was terminated and glycerol quantitated as described. Glycerol released by chemical saponification is also indicated. FIG. 1 shows that the rate of glycerol release in the presence of surfactant ⊟ was faster than that observed with $\alpha$-chymotrypsin ⊙ as the dissociating agent.

EXAMPLE 2—Serum Triglyceride Hydrolysis as a Function of Surfactant Concentration Unbuffered reconstituted serum was preincubated in the presence of 0.5 to about 4% by volume of octyl phenoxy polyethoxy ethanol (Triton X-100) for five minutes at 37° C. and then the reaction was initiated by enzyme addition (final concentration, 40 mg/ml). After 20 minutes, the reaction was terminated and glycerol quantitated as described above. Glycerol released by chemical saponification of an aliquot of the same serum sample also is indicated.

FIG. II demonstrates the stimulation of the enzyme catalyzed triglyceride hydrolysis by various concentrations of surfactant. Maximum glycerol release was observed at surfactant concentrations above 1.0%, and the extent of the enzymatic reaction was above 96% of a chemical saponification of the same serum sample.

EXAMPLE 4—Lipase Catalyzed Serum Triglyceride Hydrolysis in the Presence of Nonionic Surfactants Unbuffered reconstituted serum (Validate) and effectors were allowed to incubate at 37° C. for 5 minutes; then reactions were initiated by enzyme addition (40 mg/ml final concentration) and allowed to proceed for 20 minutes. Termination and glycerol quantitation were as described above with the results illustrated in Table II. Surfactants S-1 through S-7 are octyl phenoxy polyoxyethylenes having polyoxyethylene chains of different lengths.

TABLE II

| Surfactant | Polyoxyethylene Chain Length (n) | Glycerol Released ($\mu$ moles/ml serum) Actual | Theoretical[a] | % Recovery |
|---|---|---|---|---|
| S-1 | 7–8 | 0.78 | 0.74 | 105 |
| S-2 | 9–10 | 0.67 | 0.74 | 91 |
| S-3 | 8–9 | 0.205 | 0.8 | 89 |
| S-4 | 12–13 | 0.76 | 0.74 | 102 |
| S-5 | 30 | 0.11 | 0.80 | 13.7 |
| S-6 | 40 | 0.09 | 0.8 | 11.2 |
| S-7 | 30 | 0.061 | 1.01 | 6 |
| Nonyl Phenyl Polyglycidol | — | 0.07 | 1.2 | 6 |
| Saponin | — | 0.05 | 0.81 | 6 |

[a] As in Table I

EXAMPLE 3—Lipase Catalyzed Serum Triglyceride Hydrolysis in the Presence of Anionic Surfactants Unbuffered reconstituted serum (Validate) and effectors were allowed to incubate at 37° C. for 5 minutes; then reactions were initiated by enzyme addition (40 mg/ml final concentration) and allowed to proceed for 20 minutes. Termination and glycerol quantitation were as described above.

Anionic surfactants which stimulated serum triglyceride hydrolysis are shown in Table I. All of the bile salts stimulated relatively high extents of hydrolysis. An unpurified sample of sodium taurocholate was most effective (100% hydrolysis), but a highly purified sample of this bile salt was considerably less effective (41% hydrolysis). The unpurified sample contained glycocholic, cholic, deoxycholic and other bile acids in addition to taurocholic acid. An anionic surfactant marketed by E.I. duPont under the tradename Alkanol XC also stimulated essentially complete hydrolysis (99% hydrolysis).

As demonstrated above, nonionic octyl phenoxy polyoxyethylene surfactants demonstrate differential stimulation of serum triglyceride hydrolysis depending on the length of the polyoxyethylene chain. As the length of the chain increases, these molecules are apparently more hydrophilic and therefore less able to disrupt the hydrophobic lipoprotein complexes which activity is necessary for triglyceride hydrolysis. Surfactants with n values below 7 were not soluble in water and were not tested. Surfactants with a polyoxyethylene chain length of 7–13 units are most efficient at effecting hydrolysis.

The methods and compositions described herein for triglyceride hydrolysis are similarly useful to obtain hydrolysis glycerophospholipids. Compositions useful for such hydrolysis of comprise a compatible mixture of an enzyme preparation having phospholipid hydrolase activity and an effector which is a surfactant. For purposes of this aspect of the invention, compatibility of the enzyme preparation and the surfactant are determined using a test analagous to that described hereinabove for

TABLE I

| Additions | Glycerol Released ($\mu$ moles/ml serum) Actual | Theoretical | % Recovery |
|---|---|---|---|
| none | 0.08 | 1.43 | 6 |
| $\alpha$-chymotrypsin (20 mg/ml)[b] | — | — | 97 |
| crude bile salt mixture (2.5%)[c] | 0.8 | 0.8 | 100 |
| deoxycholate (0.5%) | 1.04 | 1.22 | 85 |
| chenodeoxycholate (0.5%) | 0.7 | 0.92 | 76 |
| cholate (2.5%) | 0.9 | 1.17 | 77 |
| glycocholate (2.5%) | 0.66 | 1.02 | 64 |
| taurocholate (1.0%) | 0.47 | 1.15 | 41 |
|  | 1.19 | 1.2 | 99 |
| Na Salt of Alkylaryl Polyether Sulfonate (1.3%) | 0.95 | 1.22 | 78 |
| sodium dodecylsulfate (1.0%) | 0.62 | 1.22 | 51 |
| N-coco Beta Amino Propionic Acid (1%) | 0.215 | 1.4 | 15 |

[a] Theoretical refers to glycerol released from a particular serum sample by saponification at 7 for 30 minutes.
[b] $\alpha$-Chymotrypsin was tested as a control during each study. The % Recovery refers to the average of all values.
[c] Taurocholate from ox bile stated to contain glycocholic, cholic, deoxycholic, and other bile acids.

similar mixtures useful in the hydrolysis of triglycerides. The following Example 5 demonstrates the utility of these methods and compositions for this purpose.

EXAMPLE 5

To one ml of serum (Validate) was added an aqueous solution comprising 22.5U of lipase from *Candida rugosa* and 1% S-4 to yield a total volume of 10 ml. The mixture was heated for 20 minutes at 37° C. Acid production was then measured titrimetrically. The results of this testing are shown in Table III below.

TABLE III

| Analyte | Serum Concentration | Potential Acid Production | Total Acid Production |
|---|---|---|---|
| | moles/ml | moles/ml | moles/ml |
| triglycerides | 0.62 | 1.86 | 6.10 |
| phospholipid | 2.2 | 4.4* | |

The foregoing indicates that the combination of enzyme and surfactant also hydrolyzes phospholipids.

The invention has been described in detail with particular reference to certain preferred embodiments thereof, but it will be understood that variations and modifications can be effected within the spirit and scope of the invention.

What is claimed is:

1. A process for hydrolyzing protein-bound triglycerides consisting of contacting in an aqueous medium protein-bound triglycerides and a reagent consisting of a compatible mixture of (i) a lipase preparation having triglyceride hydrolase activity and derived from a source selected from the group consisting of *Candida rugosa* and *Chromobacterium viscosum* (variant *paralipolyticum*); and (ii) a synthetic surfactant selected from the group consisting of salts of alkylaryl polyether sulfonates and alkoxy polyethoxy ethanols.

2. A process for hydrolyzing protein-bound triglycerides consisting of contacting in an aqueous medium protein-bound triglycerides and a reagent consisting of a compatible mixture of (i) a lipase preparation having triglyceride hydrolase activity and derived from a source selected from the group consisting of *Candida rugosa* and *Chromobacterium viscosum* (variant *paralipolyticum*); and (ii) an alkyl phenoxy polyethoxy ethanol surfactant comprising a polyoxyethylene chain of less than 20 oxyethylene units and have a hydrophilic-lipophilic balance number below about 15.

3. The process of claim 1 wherein the lipase preparation is derived from *Candida rugosa*.

4. The process of claim 1 wherein the surfactant is an alkyl phenoxy polyethoxy ethanol of from about 7 to about 13 ethoxy ethylene units.

5. The process of claim 1 wherein the surfactant is an octyl phenoxy polyethoxy ethanol.

6. In a process for assaying blood serum for total serum triglyceride in which triglycerides are first hydrolyzed to glycerol and the glycerol concentration is subsequently determined, the improvement consisting of hydrolyzing the triglycerides by contacting them in an aqueous medium with a compatible mixture consisting of (i) a lipase preparation having triglyceride hydrolase activity and derived from a source selected from the group consisting of *Candida rugosa* and *Chromobacterium viscosum* (variant *paralipolyticum*); and (ii) an effector which is a synthetic surfactant selected from the group consisting of salts of alkylaryl polyether sulfonates and alkoxy polyethoxy ethanols.

7. In a process for assaying blood serum for total serum triglyceride in which triglycerides are first hydrolyzed to glycerol and the glycerol concentration is subsequently determined, the improvement consisting of hydrolyzing the triglycerides by contacting them in an aqueous medium with a compatible mixture consisting of (i) a lipase preparation having triglyceride hydrolase activity and derived from a source selected from the group consisting of *Candida rugosa* and *Chromobacterium viscosum* (variant *paralipolyticum*); and (ii) an effector which is an alkyl phenoxy polyethoxy ethanol surfactant comprising a polyoxyethylene chain of less than 20 oxyethylene units and having a hydrophilic-lipophilic balance number below about 15.

8. The process of claim 7 wherein the lipase preparation is derived from *Candida rugosa*.

9. The process of claim 7 wherein the surfactant is an alkyl phenoxy polyethoxy ethanol of from about 7 to about 13 ethoxy ethylene units.

10. The process of claim 7 wherein the surfactant is an octyl phenoxy polyethoxy ethanol.

11. A process for hydrolyzing blood serum phospholipids comprising contacting serum containing said phospholipid and a hydrolysis mixture consisting of (i) a lipase preparation having phospholipid hydrolase activity and derived from a source selected from the group consisting of *Candida rugosa* and *Chromobacterium viscosum* (variant *paralipolyticum*); and (ii) a surfactant selected from the group consisting of salts of alkylaryl polyether sulfonates and alkoxy polyethoxy ethanols.

12. A process for hydrolyzing blood serum phospholipids comprising contacting serum containing said phospholipid and a hydrolysis mixture consisting of (i) a lipase preparation having phospholipid hydrolase activity and derived from a source selected from the group consisting of *Candida rugosa* and *Chromobacterium viscosum* (variant *paralipolyticum*); and (ii) an alkyl phenoxy polyethoxy ethanol surfactant comprising a polyoxyethylene chain of less than 20 oxyethylene units and having a hydrophilic-lipophilic balance number below about 15.

13. The process of claim 12 wherein the lipase preparation is derived from *Candida rugosa*.

14. The process of claim 12 wherein the surfactant is an alkyl phenoxy polyethoxy ethanol of from about 7 to about 13 ethoxy ethylene units.

15. The process of claim 12 wherein the surfactant is an octyl phenoxy polyethoxy ethanol.

16. An analytical element comprising at least one layer which includes as a hydrolysis composition a compatible mixture of (i) a lipase preparation having triglyceride hydrolase or phospholipid hydrolase activity and derived from a source selected from the group consisting of *Candida rugosa* and *Chromobacterium viscosum* (variant *paralipolyticum*); and (ii) an effector which is a synthetic surfactant selected from the group consisting of salts of alkylaryl polyether sulfonates and alkoxy polyethoxy ethanols.

17. An analytical element comprising at least one layer which includes as a hydrolysis composition a compatible mixture of (i) a lipase preparation having triglyceride hydrolase or phospholipid hydrolase activity and derived from a source selected from the group consisting of *Candida rugosa* and *Chromobacterium viscosum* (variant *paralipolyticum*); and (ii) an effector which is an alkyl phenoxy polyethoxy ethanol surfactant comprising a polyoxyethylene chain of less than 20 oxyethylene units and having a hydro-lipophilic balance number below about 15.

18. An analytical element for the detection of lipids in aqueous solution, said element comprising at least one layer which includes as a hydrolysis composition for protein-bound lipids a compatible mixture of (i) a lipase preparation having triglyceride hydrolase or phospholipid hydrolase activity and derived from a source selected from the group consisting of *Candida rugosa* and *Chromobacterium viscosum* (variant *paralipolyticum*); and (ii) a surfactant selected from the group consisting of salts of alkylaryl polyether sulfonates and alkoxy polyethoxy ethanols.

19. An analytical element for the detection of lipids in aqueous solution, said element comprising at least one layer which includes as a hydrolysis composition for protein-bound lipids a compatible mixture of (i) a lipase preparation having triglyceride hydrolase or phospholipid hydrolase activity and derived from a source selected from the group consisting of *Candida rugosa* and *Chromobacterium viscosum* (variant *paralipolyticum*); and (ii) an alkyl phenoxy polyethoxy ethanol surfactant comprising a polyoxyethylene chain of less than 20 oxyethylene units and having a hydrophilic-lipophilic balance number below about 15.

20. The element of claim 19 wherein the element comprises a spreading layer and a reagent layer.

21. The element of claim 19 wherein the lipase preparation is derived from *Candida rugosa*.

22. The element of claim 19 wherein the surfactant is an alkyl phenoxy polyethoxy ethanol of from about 7 to about 13 ethoxy units.

23. The element of claim 19 wherein the surfactant is an octyl phenoxy polyethoxy ethanol.

24. An analytical element for the detection of triglycerides in aqueous solution, said element comprising at least one layer which includes as a hydrolysis composition for protein-bound triglycerides a compatible mixture of (i) a lipase preparation having triglyceride hydrolase or phospholipid hydrolase activity and derived from a source selected from the group consisting of *Candida rugosa* and *Chromobacterium viscosum* (variant *paralipolyticum*); and (ii) a surfactant selected from the group consisting of salts of alkylaryl polyether sulfonates and alkoxy polyethoxy ethanols.

25. An analytical element for the detection of triglycerides in aqueous solution, said element comprising at least one layer which includes as a hydrolysis composition for protein-bound triglycerides a compatible mixture of (i) a lipase preparation having triglyceride hydrolase or phospholipid hydrolase activity and derived from a source selected from the group consisting of *Candida rugosa* and *Chromobacterium viscosum* (variant *paralipolyticum*); and (ii) an alkyl phenoxy polyethoxy ethanol surfactant comprising a polyoxyethylene chain of less than 20 oxyethylene units and having a hydrophilic-lipophilic balance number below about 15.

* * * * *